US 6,582,383 B2

(12) United States Patent
Horning

(10) Patent No.: US 6,582,383 B2
(45) Date of Patent: Jun. 24, 2003

(54) BANDAGE FOR APPLICATION OF THERAPEUTIC COLD OR HEAT TREATMENTS TO INJURIES

(76) Inventor: Larry R. Horning, 41 N. Briarcliff Rd., Mountain Lakes, NJ (US) 07046

( * ) Notice: Subject to any disclaimer, the term of this patent is extended or adjusted under 35 U.S.C. 154(b) by 0 days.

(21) Appl. No.: 09/371,314

(22) Filed: Aug. 10, 1999

(65) Prior Publication Data
US 2002/0052569 A1 May 2, 2002

(51) Int. Cl.$^7$ ................................................ A61F 13/00
(52) U.S. Cl. .................... 602/60; 602/75; 607/112; 607/114
(58) Field of Search .................. 602/60, 75; 607/108, 607/109, 110, 111–114

(56) References Cited

U.S. PATENT DOCUMENTS

| 3,871,376 A | 3/1975 | Kozak ................ 128/275.1 |
| 3,889,684 A | 6/1975 | Lebold ................ 128/402 |
| 3,900,035 A | 8/1975 | Welch et al. ........ 128/402 |
| 3,950,789 A | 4/1976 | Konz et al. .............. 2/93 |
| 4,190,054 A | 2/1980 | Brennan ............... 128/402 |
| 4,517,972 A | 5/1985 | Finch, Jr. ............. 128/156 |
| 4,556,055 A | 12/1985 | Bonner, Jr. ........... 128/82.1 |
| 4,575,097 A | 3/1986 | Brannigan et al. .... 128/402 |
| 4,592,358 A | 6/1986 | Westplate ............. 128/402 |
| 4,645,498 A | 2/1987 | Kosak ................. 604/289 |
| 4,676,247 A | 6/1987 | Van Cleve ............ 128/402 |
| 4,688,572 A | 8/1987 | Hubbard et al. ...... 128/402 |
| 4,700,706 A | 10/1987 | Münch ................. 128/403 |
| 4,753,240 A | 6/1988 | Sparks ................. 128/379 |
| 4,886,063 A | 12/1989 | Crews ................. 128/403 |
| 4,981,135 A | 1/1991 | Hardy ................. 128/402 |
| 5,005,374 A | 4/1991 | Spitler ............... 62/259.3 |
| 5,016,629 A | 5/1991 | Kanare ............... 128/402 |
| 5,065,758 A | * 11/1991 | Whitehead et al. |
| 5,069,208 A | 12/1991 | Noppel et al. ....... 128/403 |
| 5,150,707 A | 9/1992 | Anderson ........... 128/402 |
| 5,176,134 A | 1/1993 | Hudson ............... 128/402 |
| 5,179,944 A | 1/1993 | McSymytz ......... 128/403 |
| 5,304,216 A | * 4/1994 | Wallace |
| 5,336,255 A | 8/1994 | Kanare et al. ........ 607/149 |
| 5,391,198 A | 2/1995 | Cheney, III et al. .. 607/114 |
| 5,395,399 A | 3/1995 | Rosenwald ........... 107/108 |
| 5,415,624 A | 5/1995 | Williams ............... 602/21 |
| 5,466,251 A | * 11/1995 | Brunson et al. |
| 5,496,358 A | 3/1996 | Rosenwald ........... 607/108 |
| 5,507,793 A | 4/1996 | Hodges ............... 607/109 |
| 5,697,962 A | 12/1997 | Brink et al. ......... 607/108 |

* cited by examiner

Primary Examiner—Nicholas D. Lucchesi
Assistant Examiner—Lalita M. Hamilton
(74) Attorney, Agent, or Firm—Ernest D. Buff & Associates; Ernest D. Buff

(57) ABSTRACT

A bandage wrapped around a body part has a flexible central web which is generally annular in shape. At least one pouch is affixed to the central web. The pouch contains a removable temperature transference source therewithin. The bandage is especially suited for the treatment of swelling, and for use during post-operative surgeries. It is also suited for treatment of traumatic insults to various body regions, including the chest, torso, legs, arms, wrists, shoulder, head and neck, knees, thighs, ankles, jaw, chin, lower back, knee thigh and shoulder and the like.

13 Claims, 5 Drawing Sheets

BANDAGE FOR APPLICATION OF THERAPEUTIC COLD OR HEAT TREATMENTS TO INJURIES

BACKGROUND OF THE INVENTION

1. Field of the Invention

The present invention relates to a bandage for the application of therapeutic treatments to injuries; and more specifically, to a bandage useful for applying heat or cold treatments to a specific portion of the body.

2. Description of the Prior Art

It is well known that the application of heat or cold therapies provides effective relief for muscle and joint injuries. When properly applied, heat and cold treatments provide effective relief from sprains, strains, bruises, muscle trauma, and other injuries to the body. Generally, a patient seeking to apply such treatments will place ice bags, cold compresses or pads comprised of folded cloth containing ice or heat packs on injured body areas. Typically, these devices are held in place by means such as adhesive tapes, tying gauze strips or surgical dressings or by merely having the patient lie on or sit next to such compresses so that cold or heat may reach injury areas. Inasmuch as these treatments provide relief to the patient, they cause the patient to suffer from cold hands, dripping containers, tape removal, repetitive applications, immobility or the like associated with the application of such therapies. Moreover, these bandages tend to not remain in place during vigorous activity.

Numerous cylindrical type wrap configurations have been proposed in the prior art for applying heat and cold treatments to an injured body part. In some instances, these devices are open ended and may be adjusted for use by virtue of fastening means on one end thereof. For example, U.S. Pat. No. 5,065,738, describes a cold pack for treating an injury in which a cooling media, such as Blue Ice, is encased in elongate plastic closed end cylinders and inserted in parallel pockets formed in a wrapper, e.g., made of cloth with the interconnecting cloth material forming flexible hinges between the cylinders. Straps provided on the wrap enable the application of the pre-chilled cold pack to be applied to the injured area of a person. U.S. patent application Ser. No. 5,304,216 describes an ice pack apparatus with a flexible base web and having a polymeric foam web connected to a bottom surface of the base web with at least one refrigerant housing mounted to a top surface of the base web positioned over the foam web. The base web structure is formed of various lengths and has a fastener structure arranged at opposed ends of the base web to secure the structure around various appendage portions of the body. U.S. Pat. No. 3,900,035 discloses an elastic bandage having spaced, transverse pockets permanently affixed to one end of the bandage which are configured to allow elastic flexible bags to be inserted therein. The bags are constructed of latex or a similar material and filled with anti-freeze coolant solution or a heat retaining agent. In practice, the pocketed end of the bandage is wrapped about a limb and the remainder of the bandage is wrapped around the pockets to provide support and insulation. The bandage is useful, for example, to treat ankle or joint injuries in humans and animals.

In other instances, the cylindrical-shaped device may be of a continuous configuration. U.S. patent application Ser. No. 5,466,251 describes a therapeutic elastic sleeve which is formed from a wide sheet of elastic material that is permanently attached to the sides of an ice pack or other appropriate heat or coolant container. The elastic portion of the sleeve can be stretched to allow the sleeve to slip over the patient's limb and align the container with the area to be treated. The elasticity of the sleeve causes it to conform to the shape of the limb, which provides structural support to the limb and also prevents the sleeve from riding up or down, or telescoping on the limb.

In yet other instances, the device is specifically designed to treat a particular body part. For example, in U.S. Pat. No. 4,190,054 there is described an elastic bandage designed to support the face after cosmetic surgery. Openings are provided at strategic locations, such as the top of the head and adjacent to the back of the neck, in order to permit the bandage to be secured around the face of a user. These openings are provided with suitable fastening means such as VELCRO® strips, to close the bandage around the face. The bandage incorporates a number of attachment points over the surface thereof for attachment of specifically designed attachable envelopes containing a heatable or coolable fluid therein which are secured to the bandage via complementary VELCRO® strips on the outside of the bandage and on one side of the envelope. The bandage permits application of heat or cold treatment without removing the bandage from the face part.

None of these prior art configurations provides therapeutic effectiveness together with ease of use and mobility. What is needed is a device which can be used to supply heat and cold therapies and which affords complete mobility to its users. Such a device should be readily adapted for use in the treatment of traumatic injuries to various body regions and should not require removal after positioning.

SUMMARY OF THE INVENTION

In accordance with the present invention, there is provided a bandage capable of being wrapped around a body part comprising a flexible central web being generally annular in shape; and at least one pouch affixed to the central web, wherein the pouch contains a removable temperature transference source, such as refrigerant or heat, therein. Preferably, the pouch is removably affixed to the central web. The bandage may be readily adapted for the treatment of swelling, for use during postoperative surgeries or traumatic insults to various body regions, including but not limited to chest, torso, legs, arms, wrists, shoulder, head and neck, knees, thighs, ankles, jaw, chin, lower back, knee thigh and shoulder and the like.

Generally stated, the bandage has upper and lower horizontal edges and has a continuous, generally annular configuration. The bandage may be made of flexible cloth or plastic material, preferably an elastic cloth material. Pouches for the storage of cold or heat packs also made of pieces of flexible cloth or plastic material, may be fixedly or removably attached to the outside surface of the wrap structure device by fastener attachments such as VELCRO®, clips, hooks, and the like. In a preferred embodiment of the bandage, the attachment of the pouches to the wrap structure is such that the flexible cloth material is brought into direct contact with the area of the body appointed to be cooled (or heated) thereby. The pouches may be attached to the bandage either in single or multiple rows aligned parallel to the horizontal edges of the device. Optionally, the pouches may be insulated with waterproof materials, e.g., plastic, mesh, etc. to prevent leakage and may also comprise closing means such as flaps, zippers, snaps and the like to prevent cold or heat packs from falling out.

In operation, the patient inserts pre-frozen ice or heat packs into the pouches, and the bandage is secured around the injured body area. The bandage may be adjusted for individual size and comfort to achieve the most effective use without slackness or tightness. Preferably, arrangement of the pouches on the bandage is such that the cloth or other material providing for maximum temperature transference is placed in direct contact with the body part appointed to be cooled (or heated) thereby. The bandage may be produced in a variety of adult and child sizes, lengths and widths for adaptation to particular body types, injuries and for greater user comfort.

Advantageously, the bandage of the present invention offers the patient mobility for other matters by eliminating the manually burdensome need to hold cold or heat packs to injuries as well as the need for frequent changes of such packs. That is, patients may make facile pack changes with or without having to take off or substantially remove the bandage once it is wrapped around the injury area. Moreover, the bandage of the present invention is configured so that it stays in position during and after vigorous activity. As such, the present invention may be readily adapted for use in the treatment of a myriad of traumatic insults to various body regions, after post-operative surgeries and even to provide comfort in common colds and fevers.

In another aspect of the present invention there is provided a method for the application of the bandage to provide therapeutic cold or heat treatments which enables users to attend to injuries without repetitive ice or heat pack changes. This method advantageously eliminates frequent manual administration of such packs to injury areas and resulting inconveniences, such as dripping bags or containers and bandage removals.

BRIEF DESCRIPTION OF THE DRAWINGS

The invention will be more fully understood and further advantages will become apparent when reference is made to the following detailed description of the preferred embodiments of the invention and the accompanying drawings in which.

DETAILED DESCRIPTION OF THE INVENTION

The present invention relates to a bandage for the application of therapeutic heat or cold treatments to injuries, and in particular, bandages having removable pouches which contain temperature transference devices therein. More specifically, the present invention comprises a bandage capable of being wrapped around a body part comprising a flexible continuous central web being generally annular in shape; and at least one pouch affixed to the central web, wherein each pouch has a removable temperature transference source therewithin. Preferably, each of the pouches is removably affixed to the central web, and the central web is arranged in relation to the pouches so that maximum transference of temperature is provided between the pouch contents and the body part appointed for treatment. Advantageously, the removable pouches permit heat or refrigerant sources to be inserted, removed, or changed without taking off the device. This affords greater patient mobility without repetitive changes of heat or refrigerant, thereby eliminating the need for frequent manual administration of heat and cold sources to injury areas with the resulting inconveniences, such as dripping containers and bandage removals. The configuration of the bandage allows the bandage to remain securely in position, even after vigorous activity. The present invention may be readily adapted for the treatment of traumatic insults to various body regions, after post-operative surgeries and even to provide comfort for common colds and fevers.

Figure 1A:
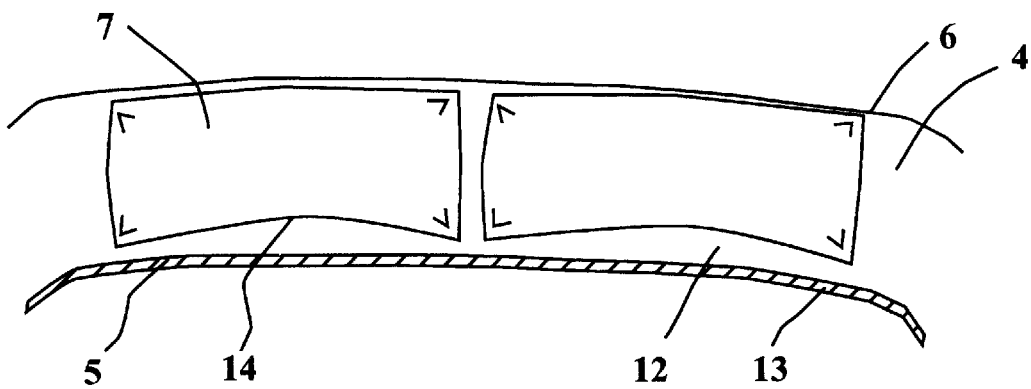
FIG. 1(a) shows a top view of the bandage of the present invention fully extended with a single row of removable pouches horizontally positioned along the length of the bandage.

The invention can be more fully understood from the following description taken in connection with the appended drawings. Turning now to FIG. 1(a) of the drawings, there is shown a top view of the bandage broken away in the middle to illustrate a fully extended device. Broadly stated, the bandage comprises a continuous central web 4 with top 5 and bottom 6 generally horizontal edges, interior 12 and exterior 13 surfaces, and a plurality of pouches 7 affixed to central web 4. Each of pouches 7 is removably affixed to the central web 4; but it is within the purview of the invention for the pouches to be permanently attached to central web 4.

Figure 2:
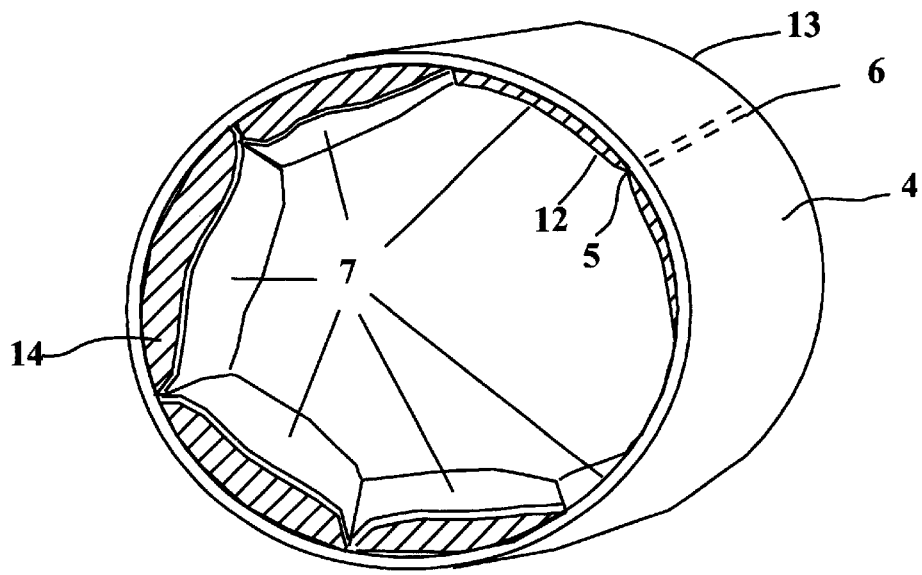
FIG. 2 shows the continuous generally annular shape of the bandage of the present invention.

In accordance with the present invention, central web 4 has a generally annular configuration. By generally annular is meant any configuration which forms a ring or a closed-loop-type configuration to form a continuous structure as illustrated in FIG. 2. Typically, the continuous configuration is formed by joining together opposing ends of a rectangular shaped central web by means which are well known in the art such as by conventional sewing, bonding, welding and the like. For example, seams may be formed by connecting opposing edges with a thermoplastic adhesive tape, or the like.

Figure 1B:
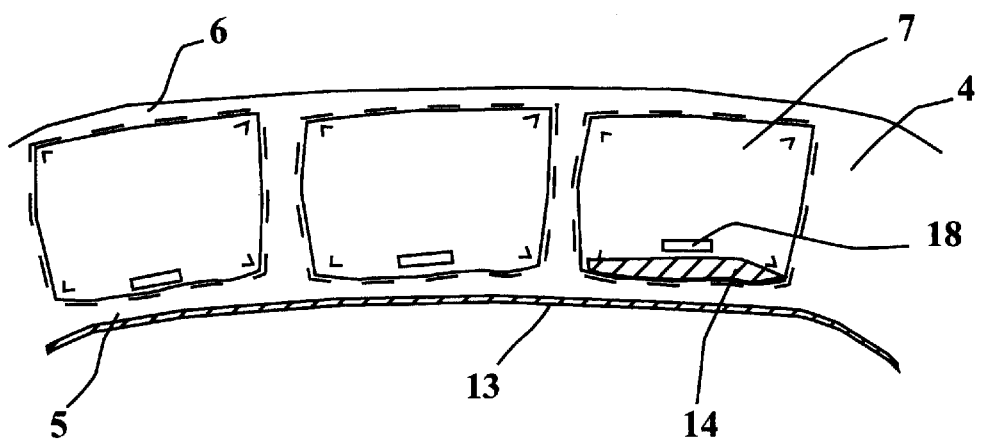
FIG. 1(b) shows a top view of an alternative embodiment of the bandage of the present invention, the pouches being arranged so that the cloth material providing maximum temperature transference is positioned towards, and in direct contact with the body part appointed to be cooled (or heated) thereby.
Figure 1C:
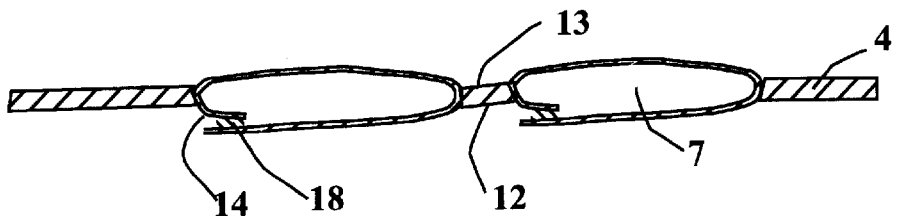
FIG. 1(c) is a side view of the embodiment of the bandage shown in FIG. 1(b)
Figure 3:
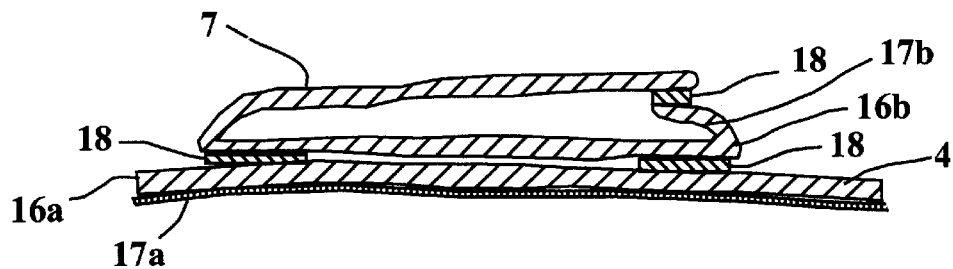
FIG. 3 is a cross-section showing layers of the central web and the pouch.

Any material which is sufficiently flexible such that it remains intact, i.e., does not exhibit any apparent fissures or cracks, when it is wrapped around a body part may be used to construct central web 4. Typically, central web 4 is constructed of a unidimensional stretch elastic cloth such as that commonly known as an ACE® bandage, a multidimensional stretch fabric such sold under the name SPANDEX™, LYCRA®, a rubber-based material such as NEOPRENE™, or a polymeric foam material. Optionally, central web may comprise either a waterproof or insulated material, or a material which is both waterproof and insulated. As illustrated in FIG. 3, central web 4 may also comprise more than one layer of material, for example, an interior insulated layer 16a surrounded by a waterproof layer 17a. Alternatively, central web 4 may comprise a plurality of insulating layers surrounded by a waterproof layer. Preferably, central web 4 contains a plurality of openings into which the pouches 7 are inserted. The side of the opening adjacent the body part being treated is composed of material having high temperature transfer capability. As shown by FIG. 1(*b*) this is readily accomplished by arranging the pouches 7 on central web 4 so that the pouches are brought into direct contact with the body part appointed for treatment.

As shown by FIG. 2, central web 4 may comprise one or more single layers of material. Optionally, each layer may be folded back on itself and seamed at either horizontal edge 5 or 6 to form a double layer of material. In this instance, the seams may be formed by conventional sewing, bonding, welding, VELCRO® strip and the like, as discussed above.

Figure 4:
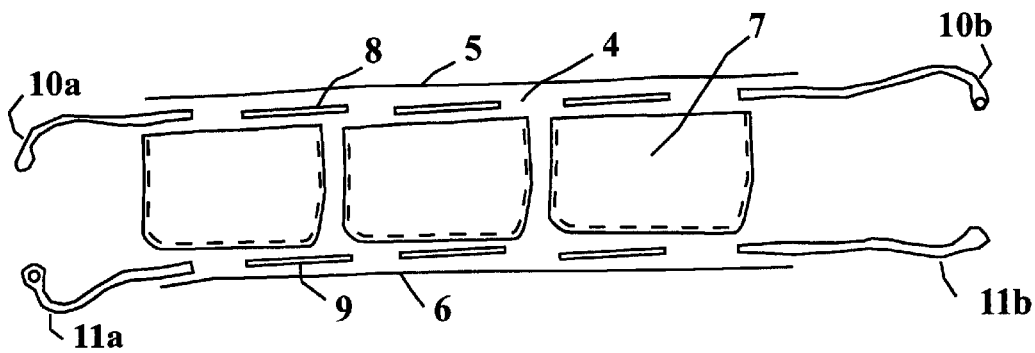
FIG. 4 is a top view of the bandage of the present invention fully extended with a cinch band at each horizontal edge.

Central web 4 may be of any size suitable for placement around at least one body part. The bandage may be fashioned such that the circumference and width of central web 4 may be readily adapted for the area to be treated. For example, a bandage suitable for use to treat the torso of a patient would be significantly larger and wider than a bandage suitable for use to treat a wrist or ankle, and the particularities of such size requirements are known and readily available to a skilled artisan. Optionally, central web 4 may have a specific geometric configuration or shape to account for the varying widths of different body parts. Thus, a wrap structure specifically designed for a knee might have a trapezoidal shape to account for the decreasing size of the leg from above to below the knee joint or a wrap designed for a hand could have a hand-type configuration to permit a patient to place his or her fingers within the wrap. Preferably, central web 4 is comprised of an elastic material which is stretched to place around the area being treated and once positioned, is allowed to contract into a snug position. In this instance, central web 4 might have a generally annular shape before placement over a portion of the body, and once positioned, could conform to the shape of the area under treatment. Thus, central web 4 can be constructed to impart a radial compressive force over the encircled portion of a body part. This is particularly suitable where it is desired to use pressure together with a temperature transference device in order to treat an injury. This also confers the benefit of allowing the bandage to remain securely in position, even after vigorous activity. In another embodiment illustrated in FIG. 4, central web 4 may have cinch bands 8 and 9 which typically, are flexible elastic straps, located adjacent to horizontal edges 5 and 6, respectively. In this configuration, central web 4 could be placed around a body part, and secured by pulling and fastening cinch band 8 by cinch band fasteners 10*a* and 10*b* and cinch band 9 by cinch band fasteners 11*a* and 11*b*. Cinch band fasteners 10*a* and 10*b* and 11*a* and 11*b* may comprise hook and loop fasteners such as VELCRO® strips, or any other type of hook, clips, buckles, lace, snap, strap or the like which will be readily evident to those skilled in the art. When cinch bands 8 and 9 are pulled into a taught position, central web 4 will generally conform to the shape of the area being treated and will remain securely positioned during repeated movement of that area. Advantageously, the choice of material (i.e. stretch or non-stretch material) used for central web 4 and cinch bands 8 and 9 can be vary varied to account for the degree of pressure which is desired for a particular injury.

The invention described herein further comprises at least one pouch 7 removably affixed to exterior surface 13 of central web 4. Pouch configurations which are contemplated include, but are not limited to, open-ended or closed jackets, pockets, closed bags and the like. Basically, any type of configuration capable of holding an object therein may be used. As previously noted, pouch 7 is removably affixed to central web 4. Pouch 7 may be affixed to central web 4 by any means suitable for attaching or fastening objects together, as for example, by hoop and loop fasteners known as VELCRO® strips, hooks, clips, buckles, laces, snaps, straps and the like. FIG. 3 illustrates a preferable embodiment wherein VELCRO® strips 18 are positioned on central web 4 and pouch 7 in opposing locations to facilitate easy fastening and removal of pouch 7. This removable feature permits a patient to remove the pouch from the device, change the temperature transference device in the pouch, and replace the pouch on the bandage without removing the bandage from the patient. In this way, the patient does not suffer from the pain associated with bandage removal, nor with dripping and wet temperature transference devices. This feature is particularly beneficial for injuries requiring alternating heat and cold treatment.

Pouch 7 may be constructed of at least one layer of material which may optionally be insulated, waterproof or a combination thereof. For example, as illustrated in FIG. 3, pouch 7 may comprise insulated layer 16*b* surrounded by waterproof layer 17*b*. Pouch 7 may be constructed of a flexible material such as the type listed above with reference to central web 4. Alternatively, pouch 7 may be constructed of a rigid material such as plastic. Optionally, pouch 7 may be an elastic material which can be expanded by stretching. Once a heat or refrigerant source is positioned therein, the material is allowed to contract, and in so doing, exerts a compressive force which holds the temperature transference source inside of pouch 7. Most preferably, the material of which pouch 7 is comprised is adapted to provide for maximum temperature transfer; and that material which is immediately adjacent the heating or cooling substance contained by the pouch is placed in direct contact with the body part appointed for treatment.

Figure 5:
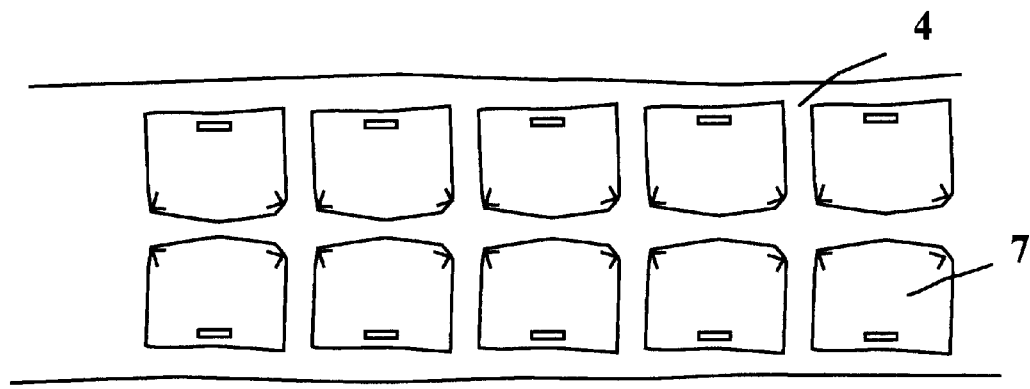
FIG. 5 is a top view showing a multiple row pouch configuration.

As previously indicated, pouch 7 may comprise a single pouch component. Typically, pouch 7 comprises a plurality of pouches which are individually positioned on or within a plurality of apertures of central web 4, or which are pre-sewn together forming a single structure which is positioned on central web 4 in a single row alignment as depicted in FIG. 1. In the latter embodiment, temperature transfer is maximized when applying central web 4 of the bandage, if pouches 7 are placed in direct contact with the body part being treated. Alternatively, pouch 7 may be positioned on central web 4 in a multiple row alignment of two or more rows or columns as illustrated in FIG. 5. Multiple row pouch alignments are useful, for example, to treat large injury areas such as the torso. This type of arrangement allows the use of a multitude of conventionally sized temperature transference devices to a large injury area which eliminates the need for large, cumbersome heat or refrigerant sources. In this arrangement, maximum temperature transfer is realized if pouches 7 are placed in direct contact with the body part being treated.

Referring again to FIG. 1(*a*), pouch 7 has an opening 14 adapted to hold a temperature transference source therein. Pouch openings may face toward, away from each other or in any such combination in their attachment to exterior surface 13 of central web 4 as would be required for the particular use of the bandage. Pouch opening 14 has a means for closing the pouch disposed thereon. Closures suitable for use in this instance include flaps, zippers, snaps, and the like and would be readily apparent to the skilled artisan. These closures prevent the temperature transference sources placed inside the pouches from falling out. FIG. 3 illustrates the use of VELCRO® as a fastener to secure the temperature transference device within pouch 7. Optionally, pouch 7 may have an additional layer of insulation to maintain the temperature required by the specific application for longer periods of time, thereby eliminating the need for frequent manual administration of the packs to the injury areas, and reducing other inconveniences associated with the bandages of the prior art, such as moisture from dripping bags or containers and frequent removal and change of the temperature transference source.

Suitable temperature transference sources for use in the present invention will be readily apparent to a skilled artisan and include ice, prepackaged cold packs such as commonly known as BLUE ICE™, hot packs, prepackaged heat or cold gels and the like. The temperature transference sources may have a rigid or flexible construction; basically, they need only be configured to fit in pouch 7 of the bandage. Preferably, the temperature transference source is a prepackaged gel which remains flexible upon heating and cooling.

In use, the bandage of the present invention is placed around the injured area which requires treatment. This can be accomplished by any conventional means such as stretching, slipping or pulling the bandage around the injured area. The bandage is then positioned by securing the cinch bands, or VELCRO® strip, or allowing the material to conform to the shape of the body part being treated, or a combination thereof. Temperature transference sources such as hot or cold packs are then inserted into the pouches. When the temperature transference source loses its efficacy, the pouch(s) can be removed from the bandage and the temperature transference source(s) changed and replaced back on the bandage, all with minimal disruption to the patient.

Figure 6:
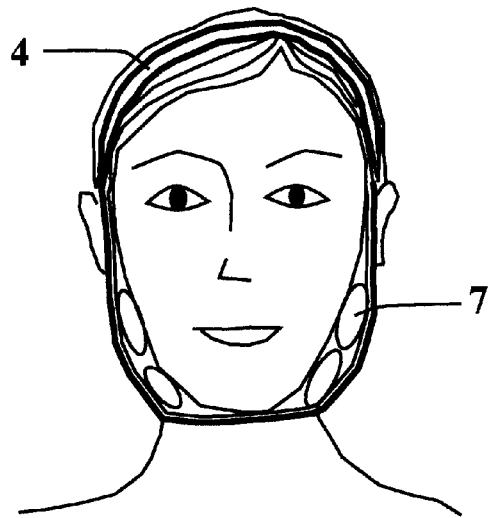
FIG. 6 is a front view of the bandage of the present invention secured around the head of a patient.

As illustrated in FIG. 6, the present invention may be adapted for dental procedures, such as wisdom teeth removal. For such applications, the bandage is preferably made of flexible cloth or plastic material, and more preferably, of a rectangular piece of elastic cloth material, and contains pouches constructed of flexible cloth or plastic material and has a plurality of pouches 7 made of flexible cloth or plastic material affixed in a single horizontal row affixed to the interior surface 23 of central web 4. In this instance, the pouches are adapted to hold ice packs, such as flexible preformed gel packs along the lower cheekbone and jawline. Maximum temperature transfer is facilitated when pouches 7 are brought into direct contact with the portion of the cheek proximate the jaw from which the wisdom teeth were removed.

Figure 7:
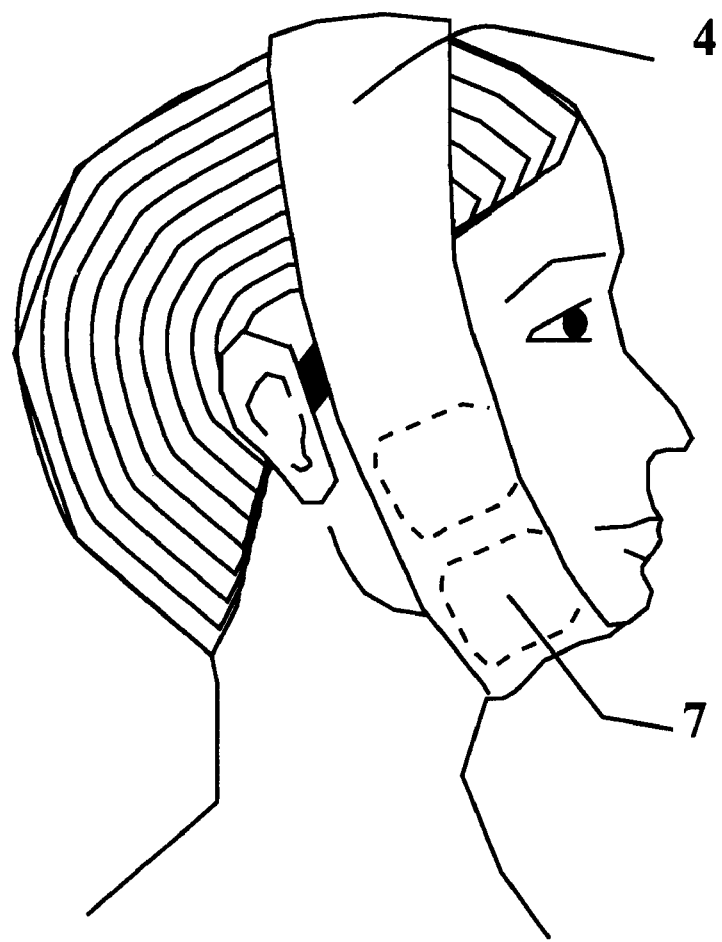
FIG. 7 is a side view of the bandage having a single row pouch configuration secured around the head of a user.

FIG. 7 illustrates a side view of bandage as adapted for dental procedures. The bandage may be stretched around the patient's head in a lengthwise fashion and the ice packs secured in the removable pouches. In the embodiment shown, the ice removable pouches have openings in the forward portions thereof for insertion and removal of the ice pacts. As the ice packs begins to lose their efficacy, they may be removed and exchanged for fresh ice packs without removing the wrap device from the head of the patient. In this way, a patient can receive continuous cooling to the injured area without further discomfort or exacerbation of the injury.

The bandage illustrated in FIG. 7 can be arranged to wrap horizontally for treatment of forehead, scalp or neck injuries, soreness, or the like. Such a bandage may also be adapted to provide for continuous cooling or heating to injuries associated with limbs, appendages, and the like.

Figure 8:
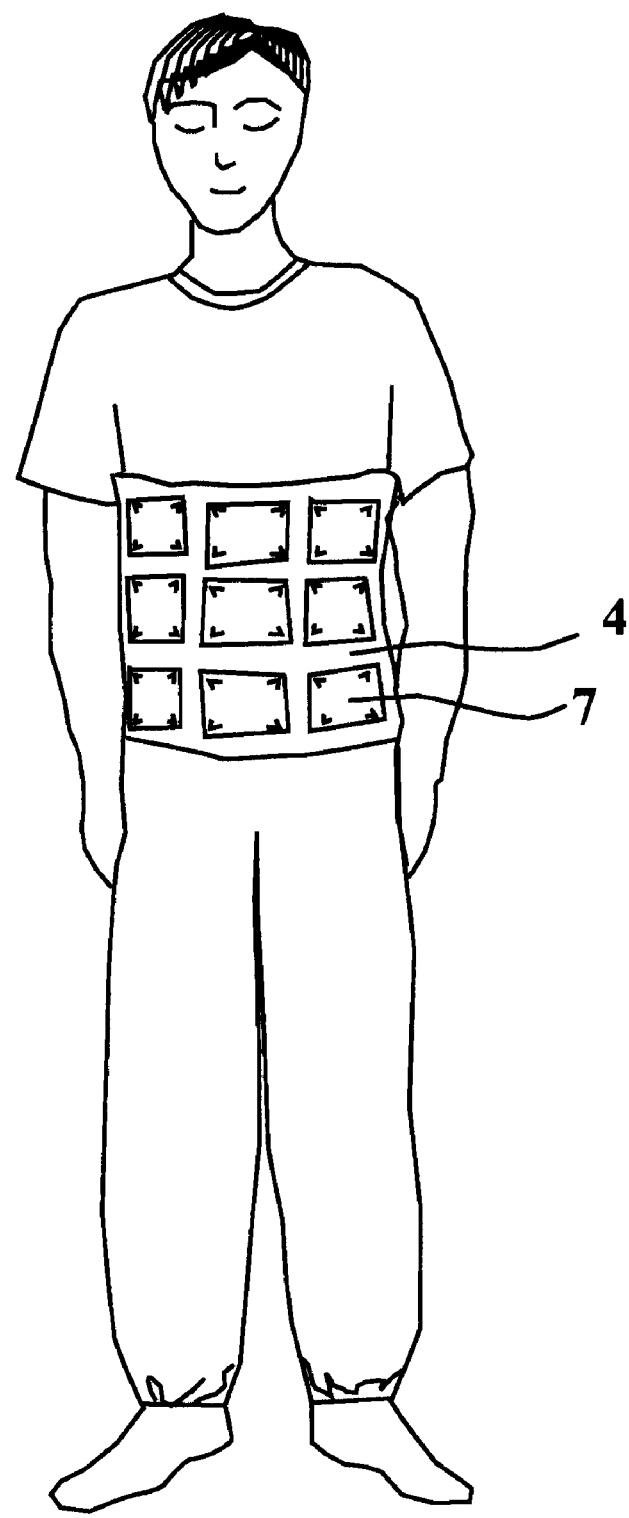
FIG. 8 is a front view of the bandage having a multiple row pouch configuration and wrapped around the torso of a patient.

Referring now to FIG. 8, there is shown the bandage adapted for use on the torso of the body including, but not limited to lower back, chest, etc. injuries or applications. The bandage has the same general configuration as with the embodiment adapted for dental procedures except that multiple rows of a plurality of pouches 7 are pre-stitched together and the pouches are positioned along the entire circumference of the wrap structure. The bandage is comprised of a stretchable fabric which may also be waterproof. When the patient slips the device over his or her head and positions it in place, the bandage will securely hold the temperature transference sources therein and will also provide overall radial compressive forces around the torso. This is particularly suitable for treating injuries in which pressure to the injured area may aid in the healing process.

Having thus described the invention in rather full detail, it will be recognized that such detail need not be strictly adhered to but that various changes and modifications may suggest themselves to one skilled in the art, all falling within the scope of the invention, as defined by the subjoined claims.

What is claimed is:

1. A bandage capable of being wrapped around a body part, comprising:
   a. a flexible central web composed of an elastic material having a continuous, generally annular configuration;
   b. at least one pouch affixed to the central web, the pouch containing a removable temperature transference source therewithin;
   c. at least a portion of such pouch being composed of material having a temperature transfer capability greater than that of said elastic material;
   d. said pouch material having the greater temperature transfer capability being positioned toward and in direct contact with said body part; and
   e. said flexible central web elastic material being insulative and having temperature transfer capability less than the said pouch material.

2. A bandage as recited in claim 1, further comprising a plurality of pouches arranged in a horizontal row on the central web, at least a portion of each of said pouches being composed of material having temperature transfer capability greater than that of said elastic material, and said portion of each of said pouches being positioned toward and in direct contact with said body part.

3. A bandage as recited in claim 1, further comprising a plurality of pouches arranged in a plurality of horizontal rows on the central web, at least a portion of each of said pouches being composed of material having temperature transfer capability greater than that of said elastic material, and said portion of each of said pouches being positioned toward and in direct contact with said body part.

4. A bandage as recited in claim 1, wherein the temperature transference device is a preformed gel pack.

5. A bandage as recited by claim 1, wherein said pouch is removably affixed to said central web.

6. A bandage as recited by claim 1, wherein said central web has a plurality of pouches affixed thereto, said web having a plurality of apertures therein, and said pouches being inserted within said apertures.

7. The use of a bandage as recited by claim 1 for treating dental trauma.

8. The use of a bandage as recited by claim 1, for treating injury or soreness associated with the neck or head.

9. The use of a bandage as recited by claim 1, for treating injury or soreness associated with the arm or leg.

10. A method of treating an injury of a body part, comprising the steps of:
   a. applying thereto a bandage comprising a flexible central web composed of an elastic, insulative material having a continuous, generally annular configuration;

b. affixing to the central web at least one pouch containing a removable temperature transference device therewithin, at least a portion of said pouch being composed of material having a temperature transfer capability greater than that of said elastic material; and c. orienting said pouch during said affixing step (b) so that said portion of said pouch is positioned toward and in direct contact with said body part.

11. A method of treating an injury, as recited by claim 10, wherein said affixing step further comprises removably affixing said pouch to said central web.

12. A method of treating an injury, as recited by claim 11, wherein said affixing step further comprises removably affixing a plurality of pouches to said elastic insulative material of said central web, at least a portion of each of said pouches being composed of material having temperature transfer capability greater than that of said elastic material, and said portion of each of said pouches being positioned toward and in direct contact with said body part.

13. A method of treating an injury, as recited by claim 12, wherein said bandage is applied so that the orientation of said central web brings said pouches into contact with said injury.

* * * * *